United States Patent

Biehler et al.

[11] 4,024,207
[45] May 17, 1977

[54] DIETHYL HYDROXYMETHYLPHOSPHONATE ESTERS, THEIR PREPARATION AND USE

[75] Inventors: Jean-Marie J. Biehler, Brunstatt; Serge L. Lecolier, Janville sur Juine; Patrice M. Le Roy, Ballancourt, all of France

[73] Assignee: Societe Nationale des Poudres et Explosifs, France

[22] Filed: June 25, 1975

[21] Appl. No.: 590,124

[30] Foreign Application Priority Data

July 4, 1974 France .............................. 74.23261

[52] U.S. Cl. .......................... 260/932; 260/2.5 AJ; 260/971
[51] Int. Cl.² ........................................... C07F 9/32
[58] Field of Search ............ 260/932, 952, 968, 971

[56] References Cited

UNITED STATES PATENTS

| 2,710,301 | 6/1955 | Morris et al. ...................... 260/932 |
| 2,989,562 | 6/1961 | Swern et al. .................... 260/932 X |
| 3,030,347 | 4/1962 | O'Brien et al. ................. 260/952 X |

Primary Examiner—Richard L. Raymond
Attorney, Agent, or Firm—Bucknam and Archer

[57] ABSTRACT

Novel diesters of diethyl hydroxymethylphosphonate of the formula:

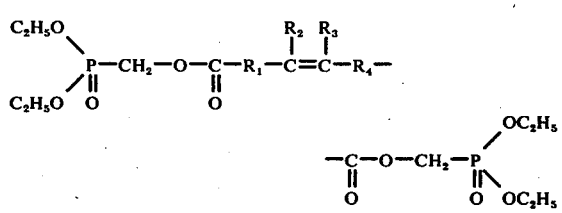

in which $R_1$ and $R_4$ are alkylene radicals $-(CH_2)_m-$ in which $m$ is 0 or an integer, $R_2$ and $R_3$ are H or alkyl radicals, the total number of carbon atoms in $R_1$, $R_2$, $R_3$ and $R_4$ being not more than 10, are described.

These diesters are valuable flameproofing agents for rigid and flexible polyurethane foams and for thermoplastic polyolefin and polyester foams.

2 Claims, No Drawings

DIETHYL HYDROXYMETHYLPHOSPHONATE ESTERS, THEIR PREPARATION AND USE

This invention is concerned with certain novel diethyl hydroxymethylphosphonate esters which are useful as flameproofing agents, particularly for polyurethane foams, with a process for their preparation and with their use as flameproofing agents.

Unreactive flameproofing agents for polyurethane foams, for example, organic phosphates which may optionally contain halogen substituents, are known. The best known representative of such unreactive agents is 2,3-dibromopropyl phosphate. However, polyurethane foams formulated with such flameproofing additives have poor aging resistance because of the tendency of the additive to exude and migrate in the course of time, and also have mediocre mechanical properties. Furthermore, the fumes evolved during the combustion of foams containing halogenated flameproofing agents are highly corrosive.

Phosphorus-containing flameproofing additives in which the molecule contains OH groups which participate in the polycondensation reaction between a polyisocyanate and a polyol which occurs in the formation of polyurethane foams are also known. These compounds are called reactive flameproofing additives. This category of flameproofing additives includes hydroxyalkyl-aminoalkyl-phosphonates, of which the best known representative has the formula:

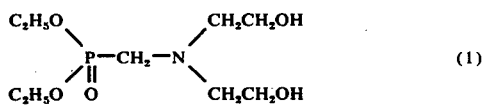

(1)

These reactive flameproofing agents are not subject to certain of the disadvantages of the unreactive additives mentioned above, namely their tendency to exude and the mediocre aging resistance of polyurethane foams containing them. However, the use of the abovementioned reactive agents is restricted to the production of rigid polyurethane foams and the combustion of foams formulated with certain of these reactive agents results in the evolution of considerable quantities of harmful fumes.

We have now found that certain esters of diethyl hydroxymethylphosphonate (which are described below) can be used as unreactive flameproofing additives which have excellent flameproofing properties and can, in particular, be incorporated into both rigid and flexible polyurethane foams. The esters in question are diesters of an unsaturated diacid and diethyl hydroxymethylphosphonate of the formula:

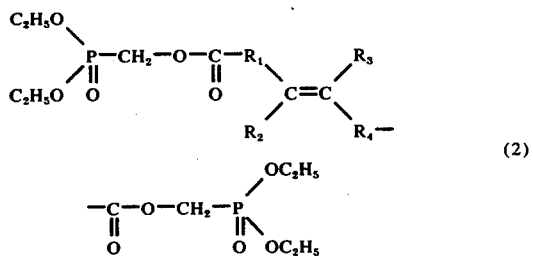

(2)

wherein $R_1$ and $R_4$, which may be the same or different, are alkylene radicals $-(CH_2)_m-$, in which $m$ is 0 or an integer, $R_2$ and $R_3$, which may be the same or different, are hydrogen or alkyl radicals, and the total number of carbon atoms of the radicals $R_1$, $R_2$, $R_3$ and $R_4$ is less than or equal to 10.

The compounds of formula (2) above are novel and constitute one aspect of the present invention.

Certain phosphorus-containing monoesters of diethyl hydroxymethylphosphonate are known, but because only a single phosphonate group is present in the molecule of such compounds, they are not of interest as flameproofing agents; in the case of such compounds, either their phosphorus content is of interest, but they are excessively volatile, or they are of sufficiently low volatility, but their phosphorus content is too low.

A preferred compound of the invention is the fumarate of diethyl hydroxymethylphosphonate, that is the compound of formula (2) in which $m=0$ and $R_2=R_3=H$ and which has the formula:

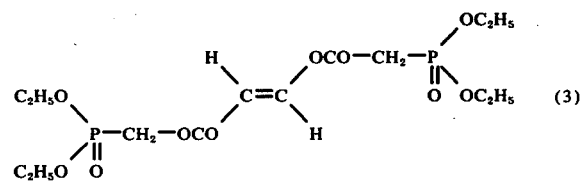

(3)

This compound is a coloured viscous oil having the following characteristics:

Infra-red an absorption band at 1.740 cm$^{-1}$, characteristic of the C = O groups and an absorption band at 1.650 cm$^{-1}$, characteristic of the C=C bond.

Nuclear magnetic resonance

The following peaks are observed: a triplet centered at 1.3 ppm, for the CH$_3$ radicals, a doublet of quadruplets centered at 4.08 ppm for the CH$_2$ groups separated from the phosphorus atom by an oxygen atom, and a doublet centered at 4.38 ppm, for the CH$_2$ groups attached to the phosphorus atom, the coupling constant J(P—CH) being 9 Hertz, and a singlet at 6.9 ppm corresponding to the hydrogen atoms attached to the C = C bond.

Phosphorus content:

Theoretical: 14.90%

Found experimentally: 14.70%.

The diesters of diethyl hydroxymethylphosphonate and, in particular, the fumarate of diethyl hydroxymethylphosphonate have proved to be excellent flameproofing agents as is shown by the results of experiments given below.

The invention also comprises a process for the preparation of the diesters according to the invention, which process comprises heating a substantially stoichiometric mixture of diethyl hydroxymethylphosphonate and a chloride of an unsaturated diacid containing from 4 to 14 carbon atoms under reflux and in the presence of pyridine and an aromatic hydrocarbon solvent.

The following example of the preparation of the fumarate of diethyl hydroxymethylphosphonate is given by way of illustration:

EXAMPLE 1

The following mixture was heated under reflux for 2 hours:

| | |
|---|---|
| Diethyl hydroxymethylphosphonate: | 2.1 mols |
| Fumaric acid dichloride: | 1 mol |

-continued

| | |
|---|---|
| Pyridine: | 2 mols |
| Benzene: | 1.5 litres. |

The reaction mixture was purified by successive washes with aqueous sodium carbonate solution and was then dried and concentrated by heating, whilst stirring, at 110° C under a vacuum of 1 mm Hg for 2 hours. The yield of purified product obtained was 75%.

The esters of diethyl hydroxymethylphosphonate according to the invention are, as stated above, useful as unreactive flameproofing additives for rigid and flexible polyurethane foams. The most effective diester for this purpose is the fumarate of diethyl hydroxymethylphosphonate.

Experiments have shown that the best results were obtained when the fumarate diester is present in polyurethane foam in an amount such that the phosphorus content of the foam is from 0.5 to 1.5% by weight.

The following example of a preferred formulation of a rigid polyurethane foam is given by way of illustration:

EXAMPLE 2

| | |
|---|---|
| Pluracol TP 440 (trimethylolpropane expxidised with propylene oxide): | 100 g |
| Methylene-diphenyl-diisocyanate: | 108.6 g |
| Dibutyl-tin dilaurate: | 0.14 g |
| N-Methylmorpholine: | 1 g |
| Rhodorsil SI.91–93 (silicone): | 1 g |
| Fumarate of diethyl hydroxymethyl-phosphonate: | 16 g (1% by weight of phosphorus) |

The polyurethane foam obtained with this formulation had a density of 50 g/liter and its critical pressure was 2.4 bars.

This foam, which will be referred to as foam A, was subjected to comparative experiments with the following polyurethane foams:

Foam B: identical to foam A, but containing 2,3-dibromopropyl phosphate, in an amount corresponding to 1% by weight of phosphorus, as the flameproofing agent.

Foam C: identical to foam A, but containing compound (1) above, diethyl dihydroxyethylaminomethylphosphonate, in an amount equal to 1% by weight of phosphorus, as the flameproofing agent.

Foam R: identical to foam A, but without flameproofing agent.

The foams A, B, C and R all had a density of 50 g/liter.

These foam samples were subjected to the "limiting oxygen index" (LOI) test according to test procedure ASTM D-2863 (see C. P. FENIMORE and F. J. MARTIN "Mod. Plastics", 44, 141, 1966). It is known that the higher the LOI index, the greater is the flameproofing power of the additive added to the polyurethane foam.

The foam samples were also subjected to the following tests:
measurement of the time required for self-ignition under a given heat flux, and
measurement of the flame propagation speed in a horizontal sample in air.
The table below gives the results obtained:

TABLE I

| Foam | LOI index | Time required for self-ignition (seconds) | Rate of combustion in air (mm/second) |
|---|---|---|---|
| A | 0.201 | 4.8 | 4.8 |
| B | 0.237 | 3.2 | — |
| C | 0.198 | 4.7 | 5.5 |
| R | 0.172 | 5.2 | 8.0 |

From the results given in Table I, it can be seen that foam A flameproofed with the fumaric diester according to the invention has better flame resistance than foam C, though both foams have the same phosphorus content. The higher value of LOI index obtained with foam B is due to the presence of a high percentage of bromine, the effect of which is additional to that of the phosphorus. However, it will be noted that in spite of this, the time required for self-ignition is markedly lower than that observed with foam A.

The mechanical properties of the above-mentioned foams A, B, C and R were also compared. These mechanical properties were determined by measuring the compressive strength of the foam samples. The critical pressure of the foam, that is to say the limiting pressure beyond which deformation of the foam is no longer elastic, was measured.

The results obtained are given in Table II below:

TABLE II

| Foam | Critical pressure CP (in bars) | Variation in CP, in %, relative to the critical pressure of foam R |
|---|---|---|
| R | 3.7 | — |
| B | 0.9 | −75% |
| C | 2.3 | −38% |
| A | 2.4 | −35% |

Table II clearly shows that the percentage decrease in the critical pressure (CP) with respect to foam R, which is considerable for foam B, for foam A compares favourably with that shown by a foam containing a reactive additive (foam C). The additive used in foam C is known for its ability to preserve good mechanical properties in foams in which it is incorporated.

In order to determine aging resistance, foams A, B, C and R were subjected to the following two tests:
aging in a dry atmosphere at 140° C for 22 hours, and
moist aging, by immersion in water at ambient temperature for 144 hours.

For both cases, the variation in critical pressure CP for each foam is expressed as a function of ageing, using the equation:

$$\frac{CPa - CPi}{CPi} \times 100$$

wherein
$CPa$ = critical pressure after aging, and
$CPi$ = critical pressure before aging.

Table III shows the results obtained after the aging tests.

TABLE III

| Foam | Deterioration in mechanical properties in % | |
|---|---|---|
| | Moist aging | Aging in a dry atmosphere |
| R | + 5 | − 6 |
| B | −32 | −11 |
| C | −11 | − 8 |

TABLE III-continued

| Foam | Deterioration in mechanical properties in % | |
|---|---|---|
| | Moist aging | Aging in a dry atmosphere |
| A | + 8 | +20 |

These results show that, contrary to foams B and C, foam A has, after aging, mechanical properties which are close, or even superior, to those of foam R.

Finally, the fumes emitted during combustion, both without a flame (pyrolysis) and with a flame (combustion), of standardised samples of foams R, C and A in an N.B.S. (National Bureau of Standards) type fume chamber were compared qualitatively and quantitatively. This fume chamber enables the specific optical density, or the dimming of a light beam which passes through the fume combustion fumes, represented by the optical density measured over unit optical path, in a chamber of unit volume for a sample of unit surface area, to be measured, as a function of time. In other words, if the specific optical density for the sample in question is called Ds, one has the following relationship:

$$Ds = D\frac{V}{AL} = \frac{V}{AL}\log\frac{Fo}{F}$$

Fo = incident light intensity
F = transmitted light intensity
V = volume of the chamber
A = surface area of the emitting sample
L = optical path.

In addition, the concentrations of hydrocyanic acid, carbon monoxide and nitrogen oxides evolved during pyrolysis or combustion of the samples were determined.

Table IV gives the results obtained:

TABLE IV

| Foam | Specific optical density | | Pyrolysis | | | Combustion | | |
|---|---|---|---|---|---|---|---|---|
| | Without flame | With flame | ppm CO | ppm HCN | ppm NO+NO$_2$ | ppm CO | ppm HCN | ppm NO+NO$_2$ |
| R | 233 | 175 | 600 | 25 | 2 | 1000 | 20 | 120 |
| C | 328 | 689 | 500 | 15 | 10 | 900 | 20 | 130 |
| A | 205 | 378 | 100 | 2 | 1 | 350 | 10 | 10 |

The measurements of the concentrations of toxic gases were carried out in the NBS fume chamber as follows. A sample of the gaseous products is taken at the centre of the chamber through colorimetric tubes specific for each gas to be analysed, by means of a calibrated syringe or calibrated squeeze-bulb of 100 ml; the tubes are graduated in ppm (Reference: "NBS Report" No. 10,328 of 27.08.1970. ASTM Publication STP 422 of 1969).

The superiority of the preferred flameproofing additive according to the invention (foam A) can be seen clearly both with respect of the amount of fumes emitted and with respect to the percentages of toxic gases evolved, which are markedly less than those observed with foams R and C.

The following example of a flexible polyurethane foam formulation is given by way of illustration:

EXAMPLE 3

| | |
|---|---|
| Napiol C 50: a branched hydroxylic polyether derived from alkylene oxides (molecular weight 3,500 ± 150), manufacturer: Rhone-Progil: | 100 g |
| Toluenediisocyanate : | 59.5 g |
| N-Methylmorpholine (catalyst): | 0.8 g |
| Dibutyl-tin dilaurate: | 0.3 g |
| Silicone: | 1.5 g |
| Water: | 4 g |
| Fumarate of diethyl hydroxymethylphosphonate: | 10.5 g (1% by weight of phosphorus) |

The density of this foam, hereinafter called foam D, was 34 g/liter. Foam D was compared with an identical reference foam which, however, did not contain any flameproofing agent.

Experiments to determine the limiting oxygen index in accordance with the standardised LOI test for flexible foams showed that foam D was 20% superior to the reference foam which had not been flameproofed.

Measurements of the time required for self-ignition have shown that foam D was non-inflammable, whilst with the reference foam, the time required for self-ignition was found to be 13.1 seconds.

It has also been established that the diethyl hydroxymethylphosphonate diesters according to the invention are able to undergo copolymerisation with olefins and the monomers of polyester resins. The flameproofing additives according to the invention can, therefore, be used for the flameproofing of thermoplastic foams of the polyolefin and polyester type.

What is claimed is:

1. Diesters of diethyl hydroxymethylphosphonate of the formula:

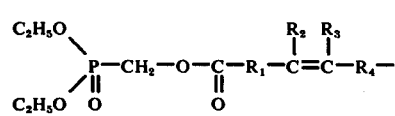

wherein R$_1$ and R$_4$ are alkylene radicals —(CH$_2$)$_m$—, in which m is 0 or an integer, R$_2$ and R$_3$ are hydrogen or alkyl radicals, and the total number of carbon atoms in the radicals R$_1$, R$_2$, R$_3$ and R$_4$ is not more than 10.

2. The compound according to claim 1, wherein m is 0 and R$_2$ and R$_3$ are both hydrogen.

* * * * *